United States Patent [19]
Oguchi et al.

[11] Patent Number: 5,773,471
[45] Date of Patent: Jun. 30, 1998

[54] TREATMENT OF OPTIC NERVE DISORDER WITH PROSTANOIC ACID COMPOUNDS

[75] Inventors: Yoshihisa Oguchi; Yukihiko Mashima; Yoshiki Hiida; Tomihiko Tanino, all of Tokyo; Ryuji Ueno, Nishinomiya; Hiroyoshi Osama; Tohru Hirato, both of Sanda, all of Japan

[73] Assignee: R-Tech Ueno, Ltd., Osaka-fu, Japan

[21] Appl. No.: 613,048

[22] Filed: Mar. 8, 1996

[30] Foreign Application Priority Data

Mar. 10, 1995 [JP] Japan ..................................... 7-051031
Jul. 14, 1995 [JP] Japan ..................................... 7-178954

[51] Int. Cl.⁶ ........................ A61K 31/215; A61K 31/19
[52] U.S. Cl. ........................ 514/530; 514/573; 514/912
[58] Field of Search ..................................... 514/573, 530

[56] References Cited

U.S. PATENT DOCUMENTS

| | | | |
|---|---|---|---|
| 5,001,153 | 3/1991 | Ueno et al. | 514/530 |
| 5,221,690 | 6/1993 | Sugiyama et al. | 514/573 |
| 5,296,504 | 3/1994 | St Jernschantz et al. | 514/530 |

FOREIGN PATENT DOCUMENTS 0503887 3/1992 France .
0308135 9/1989 Germany .

OTHER PUBLICATIONS

Medline Abstract 94120984 (1993). Azuma.
John B. Leslie, M.D. and W. David Watkins, M.D., Ph.D., *Eicosanoids in the Central Nervous System,* Journal of Neurosurgery, vol. 63, No. 5, 659–668 (1985).
A. Bar–Ilan, N. Naveh, et al., *Prostaglandin $E_2$ Changes in the Retina and Optic Nerve of an Eye with Injured Optic Nerve,* Neuroscience, vol. 45, No. 1, 221–225 (1991).
Yasumasa Goh and Junji Kishino, *Pharmacological Characterization of Prostaglandin–Related Ocular Hypotensive Agents,* Japanese Journal of Opthalmology, vol. 38, No. 3, 236–245 (1994).

*Primary Examiner*—Zohreh Fay
*Attorney, Agent, or Firm*—Sughrue, Mion, Zinn, Macpeak & Seas, PLLC

[57] ABSTRACT

The present invention provides a method for treatment of optic nerve disorder by the administration of a prostanoic acid compound in an amount effective in treatment of optic nerve disorder to a subject in need of such treatment, by which visual acuity can be recovered.

17 Claims, 9 Drawing Sheets

Fig.3 right eye before administration left eye before administration

Fig.4 right eye after administration left eye after administration

Fig.5 left eye before administration

```
                    23  19 | 23  21
                   (25)    |
              22   26  18 +17   25   17
                  (22)    (27)      (17)
         25  23  19  20 | 25   25   26  25
                 (19)         (25)
    32   32  22  17  22 ┬ 27  27   26  24  21
   (30) (30)    (23)        (29)
    35   29  19  28  30 | 31  30   29  25  27
       —(31)———————————+————————————————————
    28   30  0△  29  29 | 30  29   28  28  28
                  (31) (32)
    28   28  28  27  30 ┴ 31  27   28  28  28
                 (29)        (29)
         28  28  25  29 | 26  27   26  25
            (28)                  (28)
              28  26  28 ┬ 25  26  25
                    25  29 | 21  24
                           +
``` left eye after administration

```
                   19  17 | 23  21
                      (15)|
              14   26  26 +31   25   23
             (22)
         27   27  21  26 | 29  31   28  27
                 (23)        (27)
    28   30   30  27  26 ┬ 29  31   30  26  25
                (27)         (31)
    29   29   27  30  34 | 33  32   29  29  25
    ———————————————————+————————————————————→
    30   32  <0  31  35 | 34  33   30  30  30
                  (35)(34)
    30   28  34  35  32 ┴ 33  35   32  32  28
        (30)    (31)         (33)
         32   32  33  31 | 32  31   34   31
             (30)                  (30)
              28  28  30 ┬ 31  30  29
                    25  29 | 27  28
                           +
```

Fig.6 right eye before administration left eye before administration

Fig.7 right eye after administration left eye after administration

Fig.8 right eye before administration left eye before administration

Fig.9 right eye after administration left eye after administration

TREATMENT OF OPTIC NERVE DISORDER WITH PROSTANOIC ACID COMPOUNDS

BACKGROUND OF THE INVENTION

FIELD OF THE INVENTION

The present invention relates to the treatment of optic nerve disorder with prostanoic acid compounds.

In the structure of the optic nerve, an axon process or an optic nerve fiber, which is projected from the cell body of the optic nerve, extends in a retinal nerve fiber layer towards a papilla and enters the papilla (optic disc). There is a cribriform area of sclera at an ocular wall-penetrating site posterior to the papilla.

The outer surface of the optic nerve is enveloped by an optic nerve sheath. The anterior end of the external sheath becomes the sclera and the posterior end is fused to a periosteum of an optic canal. The internal and external sheaths are fused posterior to the cribriform area of sclera and the internal sheath further extends to communicate with a membrane which partitions the optic nerve fiber from a choroid and the sclera.

The optic nerve disorder varies in types depending on its etiology and mode of crisis. Since, however, if the axon is degenerated, the myelin sheath will be lost and when the myelin sheath is damaged, the degeneration will reach the axon before long, the disorder (degeneration or atrophia) in any part of the optic nerve results in pallidness of papilla of optic disc.

For example, when a broad disorder appears in the optic nerve cell layer (due to, for example, retinal artery occlusion), the optical nerve degenerates and atrophies ascendingly (ascending optic nerve disorder). When the degeneration appears in the axon (by various etiologies), the degeneration and atrophia proceed ascendingly and descendingly from the lesion, with pallidness of papilla in broad disorder and decrease in thickness of the optic nerve fiber layer.

The optic nerve disorder includes, for example, the followings according to etiology.

In retinal (or xanthic) optic nerve disorder, the optic nerve papilla becomes waxy yellow-white when a broad degeneration or atrophies present in a retina due to various degenerative diseases of retina. In inflammatory optic nerve disorder, which appears after an optic neuritis, papillitis, papilledema or the like, the papilla decolorizes with opacity and the margin of the papilla becomes blurring due to inflammatory exudate and its conversion into connective tissue, and also the cribriform area of sclera becomes obscure. Further, simple optic nerve disorder, axial optic nerve disorder, glaucomatous optic nerve disorder, hemianoptic optic nerve disorder and the like are also included.

Diseases which cause the optic nerve disorder include, for example, central serous chorioretinopathy, central serous chorioretinitis, hypertensive retinopathy, senile ocular fundus, arteriosclerotic retinopathy, renal retinopathy, diabetic retinopathy, retinal artery occlusion, retinal vein occlusion, retinal detachment, pigmentary retinal degeneration, retinopathy of prematurity, anemic retinopathy, leukemic retinopathy, retinochoroidal disorder by trauma, optic neuritis, papillitis, arachnoiditis, Leber's disease, myelitis and the like.

The most remarkable clinical findings in the optic nerve disorder are visual loss and contraction of visual field and therapy therefor is limited to the general tender care therapy, introduction of low frequency or direct electric current, maxillary artery infusion of fat soluble vitamin $B_1$, $B_{12}$, ATP preparation or the like and operative therapy.

Prostanoic acid is a compound having a common structural feature of and forming the skeleton of naturally occurring prostaglandins (hereinafter, prostaglandin is referred to as PG), and is shown by the following formula:

The primary PGs are classified on the basis of the structural feature of the five-membered cycle moiety into PGAs, PGBs, PGCs, PGDs, PGEs, PGFs, PGGs, PGHs, PGIs and PGJs, and also on the presence or absence of unsaturation and oxidation in the chain moiety as:

Subscript 1 - - - 13,14-unsaturated-15-OH

Subscript 2 - - - 5,6- and 13,14-diunsaturated-15-OH

Subscript 3 - - - 5,6-, 13,14- and 17,18-triunsaturated-15-OH

Further, PGFs are sub-classified on the basis of the configuration of a hydroxy group at the position 9 into α (hydroxy group is in the alpha configuration) and β (hydroxy group is in the beta configuration).

Compounds having an oxo group at the position 15 in place of the hydroxy group are known. In addition, some of the prostanoic acid compounds are known to have intraocular pressure lowering action.

Up to now, there has been no satisfactory means to relieve the above described optic nerve disorder. Accordingly, the present inventors have conducted extensive studies on the treatment of the above described optic nerve disorder.

While etiology of the optic nerve disorder is variegated, in essence, it can be said that visual loss and contraction of visual field are resulted from degeneration and atrophia of the optic nerve. Therefore, the present inventors forwarded the studies from the view point that when damaged visual acuity or visual field in a patient of optic nerve disease is recovered, the optic nerve disorder may be said to be relieved. For example, Leber's disease is a hereditary optic nerve disorder in which the patient is attacked by a sudden binocular visual disorder (or visual loss) at about 20 years old. It is believed that the cause is congenital chiasmal oppression. The onset is frequently sudden, arises in the form of acute retrobulbar optic neuritis, soon proceeds to axial optic nerve disorder and simple optic nerve disorder, and visual acuity rapidly drops usually within several months. In brief, a clear correlation exists between the visual loss and optic nerve disorder in Leber's disease. Accordingly, when damage in visual acuity in Leber's disease is relieved, the optic disorder itself can be judged to be relieved.

From the above view point, the present inventors investigated various compounds seeking compounds which are capable of relieving optic nerve disorder, and as the result, discovered the fact that the prostanoic acid compounds have unexpectedly excellent activity improving optic nerve, which fact lead them to the present invention.

SUMMARY OF THE INVENTION

In a first aspect, the present invention provides a method for treatment of optic nerve disorder which comprises administering, to a subject in need of such treatment, a prostanoic acid compound in an amount effective in treatment of optic nerve disorder.

In a second aspect, the present invention provides a use of a prostanoic acid compound for the manufacture of a medicament for treatment of optic nerve disorder.

In a third aspect, the present invention provides a pharmaceutical composition for treatment of optic nerve disorder comprising a prostanoic acid compound in association with a pharmaceutically acceptable carrier, diluent or excipient.

DETAILED DESCRIPTION OF THE INVENTION

The present invention provides a method for treatment of optic nerve disorder which comprises administering, to a subject in need of such treatment, a prostanoic acid compound in an amount effective in treatment of optic nerve disorder.

Nomenclature

Nomenclature of the prostanoic acid compounds herein is based on the numbering system of prostanoic acid represented by the formula (A).

While the formula (A) shows a basic skeleton having twenty carbon atoms, the compounds referred to in the present invention are not limited to those having the same number of carbon atoms. The carbon atoms in the formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When the number of carbon atoms is decreased in the α-chain, the number is deleted in order starting from the position 2 and when the number of carbon atoms is increased in the α-chain, compounds are named as substituted derivatives having respective substituents at the position 1 in place of carboxy group (C-1). Similarly, when the number of carbon atoms is decreased in the ω-chain, the number is deleted in order starting from the position 20 and when the number of carbon atoms is increased in the ω-chain, compounds are named as substituted derivatives having respective substituents representing 21st carbon atom and so forth at the position 20. Stereochemistry of the compounds is the same as that of above formula (A) unless otherwise specified.

While PGDs, PGEs and PGFs, for example, have a hydroxy group on the carbon atom at the position 9 and/or 11, in the present invention the compounds include those having a group other than a hydroxyl group at the position 9 and/or 11. In the nomenclature, such compounds are referred to as 9-dehydroxy-9-substituted compounds or 11-dehydroxy-11-substituted compounds.

As described above, the nomenclature of the prostanoic acid compounds is based on the formula of prostanoic acid. When these compounds have a the same moiety as that in PGs, these may be named utilizing the abbreviation "PG" for simplification purpose. These compounds can also be named according to the IUPAC naming system. For example, 13,14-dihydro-15-keto-16R,S-fluoro-PGE$_2$ is (Z)-7-{(1R,2R,3R)-3-hydroxy-2-[(4R,S)-4-fluoro-3-oxo-1-octyl]-5-oxocyclopentyl}-hept-5-enoic acid; 13,14-dihydro-15-keto-20-ethyl-11-dehydroxy-11R-methyl-PGE$_2$ methyl ester is methyl 7-{1R,2S,3S)-3-methyl-2-[3-oxo-1-decyl]-5-oxocyclopentyl}-hept-5-enoate; 13,14-dihydro-6,15-diketo-19-methyl-PGE$_2$ ethyl ester is ethyl 7-{(1R,2S,3S)-3-hydroxy-2-(7-methyl-3-oxo-1-octyl)-5-oxocyclopentyl}-6-oxoheptanoate; 13,14-dihydro-15-keto-20-ethyl-PGF$_2$α isopropyl ester is isopropyl (Z)-7-[(1R,2R,3R,5S)-3,5-dihydroxy-2-{3-oxo-1-decyl)cyclopentyl]-hept-5-enoate; 13,14-dihydro-15-keto-20-methyl-PGF$_2$α methyl ester is methyl (Z)-7-[(1R,2R,3R,5S)-3,5-dihydroxy-2-{3-oxo-1-nonyl}cyclopentyl]-hept- 5-enoate.

Preferred Embodiments

The preferred prostanoic acid compounds used in the present invention have a characteristic that the carbon atom at the position 15 form a carbonyl (i.e. 15-keto) group. The compounds include 15-keto-PG$_1$s which have a single bond between carbon atoms at the positions 5 and 6, 15-keto-PG$_2$s which have a double bond between carbon atoms at the positions 5 and 6, 15-keto-PG$_3$s which have double bonds between carbon atoms at the positions 5 and 6 as well as carbon atoms at the positions 17 and 18.

Examples of the compounds include esters at the terminal carboxy group in the α-chain of the prostanoic acid, pharmaceutically or physiologically acceptable salts, compounds having a double bond between carbon atoms at the positions 2 and 3 or a triple bond between carbon atoms at the positions 5 and 6, respectively, compounds having substituent(s) on carbon atom(s) at the position 3, 6, 16, 17, 19 and/or 20 and compounds having a lower alkyl group or a hydroxy(lower)alkyl group at the position 9 and/or 11 in place of the hydroxy group.

Substituents which may be present on the carbon atom at the position 3, 17 and/or 19 include, for example, lower alkyl of 1 to 4 carbon atoms, particularly methyl and ethyl. Substituents on the carbon atom at the position 16 include, for example, lower alkyl such as methyl, ethyl and the like; hydroxy; halogen atom such as chlorine, fluorine and the like; aryloxy such as trifluoromethylphenoxy and the like. Substituents on the carbon atom at the position 20 include saturated and unsaturated lower alkyl such as C$_{1-4}$ alkyl, lower alkoxy such as C$_{1-4}$ alkoxy and lower alkoxy(lower) alkyl such as C$_{1-4}$ alkoxy-C$_{1-4}$ alkyl. Substituents on the carbon atom at the position 6 include oxo group forming carbonyl. Stereochemistry of compounds having any hydroxy, lower alkyl or lower(hydroxy)alkyl substituent on the carbon atom at the position 9 and/or 11 may be alpha, beta or a mixture thereof.

Said compounds may have a substituent such as alkoxy, phenoxy or phenyl or the like at the end of the omega chain where the chain is shorter than the primary PGs.

Preferred compounds have a lower alkyl group such as methyl, ethyl and the like on the carbon atom at the position 20.

A group of preferred compounds used in the present invention have the formula:

(I)

wherein X and Y are hydrogen, hydroxy, halogen, lower alkyl, hydroxy(lower)alkyl or oxo with the proviso that at least one of X and Y is a group other than hydrogen and that the five-membered ring may have at least one double bond, A is COOH, a salt or ester thereof, B is —$CH_2$—$CH_2$—, —CH=CH, or —C≡C—, Z is wherein $R_3$ is lower alkyl or hydrogen, $R_1$ is a bivalent saturated or unsaturated, lower or medium aliphatic hydrocarbon residue which is unsubstituted or substituted with halogen, oxo or aryl, $R_2$ is a saturated or unsaturated, lower or medium aliphatic hydrocarbon residue which is unsubstituted or substituted with oxo, hydroxy, halogen, lower alkoxy, lower alkanoyloxy, cyclo(lower)alkyl, aryl or aryloxy.

In the above formula, the term "unsaturated" in the definitions for $R_1$ and $R_2$ is intended to include at least one optionally more double bond and/or triple bond isolatedly, separately or serially present between carbon atoms of the main and/or side chains. According to usual nomenclature, an unsaturation between two serial positions is represented by denoting the lower number of the said two positions, and an. unsaturation between two distal positions is represented by denoting both of the positions. Preferred unsaturation is a double bond at the position 2 and a double or triple bond at the position 5.

The term "lower or medium aliphatic hydrocarbon residue" or "medium aliphatic hydrocarbon residue" refers to a straight or branched chain hydrocarbonyl group having 1 to 14 carbon atoms for the lower or medium group or 5 to 14 carbon atoms for the medium group, respectively, (and for any side chain, 1 to 3 carbon atoms being preferred). It is preferred that $R_1$ has 2 to 8 and particularly 4 to 8 carbon atoms and $R_2$ has 1 to 9 and particularly 2 to 7 carbon atoms.

The term "halogen" or "halo" denotes fluoro, chloro, bromo and iodo.

The term "lower" is intended to include a group having 1 to 6 carbon atoms unless otherwise specified.

The term "lower alkyl" as a group or a moiety in a group includes saturated hydrocarbon groups of straight or branched chain having 1 to 6 carbon atoms, for example, methyl, ethyl, propyl, isopropyl, butyl, isobutyl, t-butyl, pentyl and hexyl.

The term "lower alkoxy" refers to the group lower-alkyl-O-phenyl wherein lower alkyl is as defined above.

The term "hydroxy(lower)alkyl" refers to lower alkyl as defined above which is substituted with at least one hydroxy group and includes, for example, hydroxymethyl, 1-hydroxyethyl, 2-hydroxyethyl and 1-methyl-1-hydroxyethyl.

The term "lower alkanoyloxy" refers to a group of the formula: RCO—O— wherein RCO— is an acyl group formed by oxidation of a lower alkyl group as defined above, for example, acetyl.

The term "cyclo(lower)alkyl" refers to a cyclic group formed by cyclization of a lower alkyl group as defined above.

The term "aryl" includes aromatic carbocyclic or heterocyclic (preferably monocyclic) groups which may be substituted, for example, phenyl, tolyl, xylyl and thienyl. Examples of substituents are halogen and halogen-substituted lower alkyl wherein halogen and lower alkyl are as defined above.

The term "aryloxy" refers to a group of the formula: ArO- wherein Ar is aryl as defined above.

Suitable salt of the calboxy group represented by A includes pharmaceutically acceptable salts. The term "pharmaceutically" is used interchangeably with the term "physiologically".

Suitable "pharmaceutically acceptable salts" includes conventional non-toxic salts, and may be a salt with an inorganic base, for example an alkali metal salt (sodium salt, potassium salt, etc.) and an alkaline earth metal salt (calcium salt, magnesium salt, etc.), ammonium salt, a salt with an organic base, for example, an amine salt (for example, methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt, caffeine salt, etc.), a basic amino acid salt (e.g. arginine salt, lysine salt, etc.), tetraalkyl ammonium salt and the like. These salts can be prepared, for example, by the conventional neutralization process of the corresponding acid and base or by salt interchange.

Examples of the esters are aliphatic esters including, for example, lower alkyl ester such as methyl ester, ethyl ester, propyl ester, isopropyl ester, butyl ester, isobutyl ester, t-butyl ester, pentyl ester, 1-cyclopropylethyl ester, etc., lower alkenyl ester such as vinyl ester, allyl ester, etc., lower alkynyl ester such as ethynyl ester, propynyl ester, etc., hydroxy(lower)alkyl ester such as hydroxyethyl ester, lower alkoxy(lower)alkyl ester such as methoxymethyl ester, 1-methoxyethyl ester, etc., and aromatic esters, for example, optionally substituted aryl ester such as phenyl ester, tolyl ester, t-butylphenyl ester, salicyl ester, 3,4-di-methoxyphenyl ester, benzamidophenyl ester etc., aryl (lower)alkyl ester such as benzyl ester, trityl ester, benzhydryl ester, etc. These esters can be prepared, for example, by the conventional esterification reaction of the corresponding acid and alcohol or by transesterification.

Preferred examples of the group A include —COOH, —$COOCH_3$, —$COOCH_2CH_3$ and —$COOCH(CH_3)_2$.

The configuration of the ring and the α- and/or ω-chain in the above formula (I) may be the same as or different from that in the primary PGs. However, the present invention also includes a mixture of a compound having a primary configuration and that of an unprimary configuration.

Preferred prostanoic acid compounds in the present invention include compounds of 15-keto type or 15-keto-PGs, compounds of 13,14-saturated type or 13,14-dihydro-PGs, compounds of 20-extended type or 20-alkyl-substituted-PGs, particularly those extended by 1–4 carbon atoms, type F PGs and so on.

Examples of the typical compounds of the present invention are 15-keto-20-lower-alkyl-PG(A, B, C, D, E or F)s and their Δ²-derivatives, 3R,S-methyl-derivatives, 6-keto-derivatives, 5R,S-fluoro-derivatives, 5,5-difluoro-derivatives, 16R,S-methyl-derivatives, 16,16-dimethyl-derivatives, 16R,S-fluoro-derivatives, 16,16-difluoro-derivatives, 16-phenyl-17,18 19 20-tetranor-derivatives, 17S-methyl-derivatives, 17R,S-fluoro-derivatives, 17,17-difluoro-derivatives, 17-phenyl-18,19,20-trinor-derivatives and 19-methyl-derivatives.

Typical examples of particularly preferred compounds are 15-keto-PGs, particularly -PGFs, 13,14-dihydro-15-keto-PGs, particularly -PGFS, 13,14-dihydro-15-keto-20-lower-alkyl(particularly ethyl)-PGs, particularly -PGFs and the like.

Among the prostanoic acid compounds of the present invention, 15-keto-PG compounds may be in the keto-hemiacetal equilibrium by forming a hemiacetal between hydroxy group at the position 11 and ketone at the position 15.

The proportion of the both tautomeric isomers, when present, varies depending on the structure of the rest of the molecule or kind of any substituent present and, sometimes, one isomer may predominantly be present as compared with the other. However, in this invention, it is to be appreciated that the compounds used in the invention include both isomers. Further, while the compounds used in the invention may be represented by a structure or name on the basis of keto-form regardless of the presence or absence of the isomers, it is to be noted that such structure or name does not intend elimination of the hemiacetal type of compounds.

In the present invention, any of the individual tautomeric isomers, a mixture thereof, or optical isomers, a mixture thereof, a racemic mixture, and other isomers such as steric isomers can be used in the same purpose.

Some of the compounds used in the present invention may be prepared by the method disclosed in Japanese Patent Publication (unexamined) Nos. A-2-108 and A-2-96528. Alternatively, in general, these compounds may be prepared by a process analogous to those described in the above publications or a like process in which the synthesis of the ring moiety is modified using known processes.

A practical preparation of the 13,14-dihydro-15-keto compounds involves the following steps: The Collins oxidation of commercially available (−)-Corey lactone as the starting material gives the corresponding aldehyde, which is reacted with dimethyl (2-oxoalkyl)phosphate anion to give an α,β-unsaturated ketone. The reduction of the unsaturated ketone gives the corresponding saturated ketone, which, after protection of the carbonyl group of the ketone by a diol towards the corresponding ketal, is subjected to elimination of the p-phenylbenzoyl group to give the corresponding alcohol. The newly generated hydroxy group is protected with dihydropyran to give the corresponding tetrahydropyranyl ether. According to the above process, a precursor of PGs wherein the ω-chain is a 13,14-dihydro-15-keto-alkyl group is prepared.

Using the above tetrahydropyranyl ether, 6-keto-PG$_1$s having may be prepared by the following steps: The above tetrahydropyranyl ether is reduced with, for example, diisobutyl aluminum hydride to give the corresponding lactol, which is reacted with a ylide generated from (4-carboxybutyl) triphenyl phosphonium bromide to give a carboxylic acid. After esterification, the product is subjected to the Jones oxidation and the protecting groups are removed.

Furthermore, PG$_2$s having may be prepared by the following steps: The above tetrahydropyranyl ether is reduced to give the corresponding lactol, which is reacted with a ylide generated from (4-carboxybutyl)triphenyl phosphonium bromide to give a carboxylic acid. After esterification, the product is subjected to the Jones oxidation and the protecting groups are removed.

Using the above tetrahydropyranyl ether as the starting material, PG$_1$s having may be prepared by using the same process as that for preparing PG$_2$s having and subjecting the resultant compound to catalytic reduction i order to reduce the double bond between the positions 5 and 6, followed by removal of the protective groups.

The synthesis of 5,6-dehydro-PG$_2$s having as the hydrocarbon chain at the positions 5, 6 and 7 may be carried out by capturing a copper enolate, formed by 1,4-addition of a monoalkyl copper complex or a dialkyl copper complex of the following formulae:

to 4R-t-butyldimethylsilyloxy-2-cyclopenten-1-one, with 6-alkoxycarbonyl-1-iodo-2-hexyne or a derivative thereof.

As the synthesis of PGs having a methyl group at the position 11 in place of hydroxy, 11-dehydroxy-11-methyl-PGE-type compounds can be prepared by reacting a dimethyl copper complex with PGA-type compound obtained by subjecting 9-hydroxy-11-tosylate to the Jones oxidation. Alternatively, 11-dehydroxy-11-methyl-PGE-type compounds can be prepared by converting the alcohol, obtained by eliminating p-phenylbenzoyl, into the corresponding tosylate, treating the product with DBU to form an unsaturated lactone, converting it into a lactol, introducing the α-chain by Wittig reaction, oxidizing the alcohol (the position 9) thus produced to give PGA-type compound, and reacting the product with dimethyl copper complex. Upon reduction with, for example, sodium borohydride, this gives 11-dehydroxy-11-methyl-PGF-type compounds.

As the synthesis of PGs having a hydroxymethyl group at the position 11 in place of hydroxy, 11-dehydroxy-11-hydroxymethyl-PGE-type compounds are obtained by a benzophenone-sensitized photoaddition of methanol to PGA-type compounds. Upon reduction with, for example, sodium borohydride, this gives 1-dehydroxy-11-hydroxymethyl-PGF-type compounds.

The synthesis of 16-fluoro-PGs can be conducted by using dimethyl(3-fluoro-2-oxoalkyl) phosphate anion in the production of α,β-unsaturated ketone. Also, 19-methyl-PGs can be obtained by using dimethyl(6-methyl-2-oxoalkyl) phosphate anion. For 17-phenyl-18,19,20-trinor-PGs, dimethyl (4-phenyl-2-oxobutyl) phosphate anion can be used.

The synthetic route for the compounds used in the present invention is not limited to those described above and may vary using different protecting, oxidizing and/or reducing method. Specific examples of the syntheses of prostanoic acid compounds can be found in Japanese Patent Publication (unexamined) Nos. A-1-151552, A-2-108, A-2-96528 and A-2-96529.

The compounds used in the present invention may be used as a medicine for animals and human beings and usually applied systemically or locally by such methods as ophthalmic administration, oral administration, intravenous injection (including instillation), subcutaneous injection, suppository and the like. Particularly preferred method is ophthalmic administration. While the dosage will vary depending on the particular animal or human patient, age, body weight, symptom to be treated, desired therapeutic effect, administration route, term of treatment and the like, satisfactory effects will be obtained with the dosage of 0.01–100 μg/eye administered locally or 0.001–500 mg/kg administered systemically in 2 to 4 divided doses a day or as a sustained form.

The ophthalmic composition used according to the invention includes ophthalmic solution, ophthalmic ointment and the like. The ophthalmic solution can be prepared by dissolving an active ingredient in a sterile aqueous solution such as a physiological saline or a buffered solution, or as a combination of a solid and a solution for dissolving said solid to make a ready-to-use preparation. The ophthalmic ointment can be prepared by mixing an active ingredient with an ointment base.

The solid composition for oral administration used according to the present invention includes tablets, troches, buccals, capsules, pills, powders, granules and the like. The solid composition contains one or more active substances in admixture with at least one inactive diluent, for example, lactose, mannitol, glucose, hydroxypropyl cellulose, fine crystalline cellulose, starch, polyvinyl pyrrolidone, magnesium aluminate metasilicate. The composition may contain additives, in addition to the inactive diluent, for example, lubricants,for example, magnesium stearate, a disintegrator, for example, cellulose calcium gluconates, stabilizers, for example, α-, β- or γ-cyclodextrins, etherated cyclodextrins such as dimethyl-α-, dimethyl-β-, trimethyl-β-, or hydroxypropyl-β-cyclodextrins, branched cyclodextrins, for example, glucosyl- or maltosyl-cyclodextrins, formyl cyclodextrins, sulfur-containing cyclodextrins, misoprotols or phospholipids. The above cyclodextrins may increase the stability of the compounds by forming an inclusion compounds. The stability may be often increased by forming lyposome with phospholipids. Tablets and pills may be coated with an enteric or gastroenteric film, for example, white sugar, gelatin, hydroxypropyl cellulose, hydroxypropyl methyl cellulose phthalates and the like, if necessary, and furthermore they may be covered with two or more layers. Additionally, the composition may be in the form of capsules made of an easily disintegrable substance such as gelatin. The composition may be in the form of buccals, when an immediate effect is desired. For this purpose, base e.g. glycerine, lactose may be used.

The liquid compositions for oral administration includes pharmaceutically acceptable emulsions, solutions, suspensions, syrups, elixirs and the like. They may contain a commonly used inactive diluent, for example, purified water or ethanol. The composition may contain additives, for example, wetting agents, suspending agents as well as sweeteners, flavors, perfumes and preservatives.

The composition for oral administration may be in the form of sprays which may contain one or more active ingredients and which can be prepared according to the well known methods.

The injection of this invention for non-oral administration includes sterile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oils such as olive oil, alcohols, such as ethanol and polysorbates. The composition may contain other additives, such as preservatives, wetting agents, emulsifying agents, dispersing agents and the like. These are sterilized by, for example, filtration through a bacteria-retaining filter, compounding with a sterilizer, gas sterilization or radiation sterilization. These can be prepared by dissolving in a sterilized water or a sterilized solvent for injection directly before use.

Another formulation according to the present invention is a rectal or vaginal suppository. This can be prepared by mixing at least one active compound according to the invention with a suppository base which can be softened such as cacao butter. Optionally, nonionic surfactant having an appropriate softening temperature may be added for improving absorption.

Since the compounds used in the present invention have an excellent activity in treatment of optic nerve disorder such as recovery or improvement of visual acuity or visual field as indicated by test examples described after, these can be used for preparing a medicament for treating, such as relieving, various optic nerve disease including, for example, central serous chorioretinopathy, central serous chorioretinitis, renal retinopathy, diabetic retinopathy, retinal artery occlusion, retinal vein occlusion, retinal detachment, pigmentary retinal degeneration, retinopathy of prematurity, papillitis, arachnoiditis, Leber's disease, myelitis and the like.

As used herein, the term "treatment" or "treating" refers to any means of control of a disease in a mammal, including prevention of the disease, cure of the disease, relief of the disease and arrestation or relief of development of the disease.

EXAMPLES

A more complete understanding of the present invention can be obtained by reference to the following Examples which are provided herein for purpose of illustration only and are not intended to limit the scope of the invention.

Example 1

(Method)

A patient (male, 26 years old, Leber's disease) received twice a day administration of a Rescula eye drops (0.12%) for 8 weeks.

(Results)

Objective findings: Recovery of visual acuity (V.A.) was clearly observed.

TABLE 1

|  | right eye | left eye |
| --- | --- | --- |
| V.A. before administration (corrected eye) | 0.04 | 0.05 |
| V.A. after administration (corrected eye) | 0.08 | 0.06 |

Subjective findings: The patient felt that he could see easier as compared with himself before treatment. (Stereoscopic vision became easier.)

When thirteen months have passed after starting the administration, recovery of visual acuity in only right eye to 0.3 was observed.

The Rescula eye drops (0.12%) contained 0.12% of 13,14-dihydro-15-keto-20-ethyl-PGF$_2\alpha$ isopropyl ester (generic name: Isopropyl Unoproston).

Example 2

A patient (female, 69 years old) received twice a day administration of the same Rescula eye drops as that in Example 1 for 4 weeks.

Conditions of visual fields before and after administration were measured using a Humphrey perimeter. The obtained "global index" are shown in Table 2.

Intraocular pressures (I.O.P.) before the administration were 18 mm Hg in both right and left eyes and I.O.P. after the administration were 18 mm Hg in right eye and 20 mm Hg in left eye. Therefore almost no effect was present in respect of I.O.P.

TABLE 2

| (Global Index) | | |
| --- | --- | --- |
|  | right eye before administration | left eye before administration |
| MD* | −5.74 DB | −7.28 DB |
| CPSD** | 0.00 DB | 7.44 DB |
|  | right eye after administration | left eye after administration |
| MD* | −1.33 DB | −1.03 DB |
| CPSD** | 2.68 DB | 3.04 DB |

*MD: mean deviation (mean of depression from the normal value for age group in sensitivity, indicating depression in total visual field)
**CPSD: corrected pattern of standard deviation (PSD corrected by SF, indicating local depression); PSD means deviation of sensitivity from the normal pattern. SF means scattering of found thresholds in twice measured site.

Figure 1:
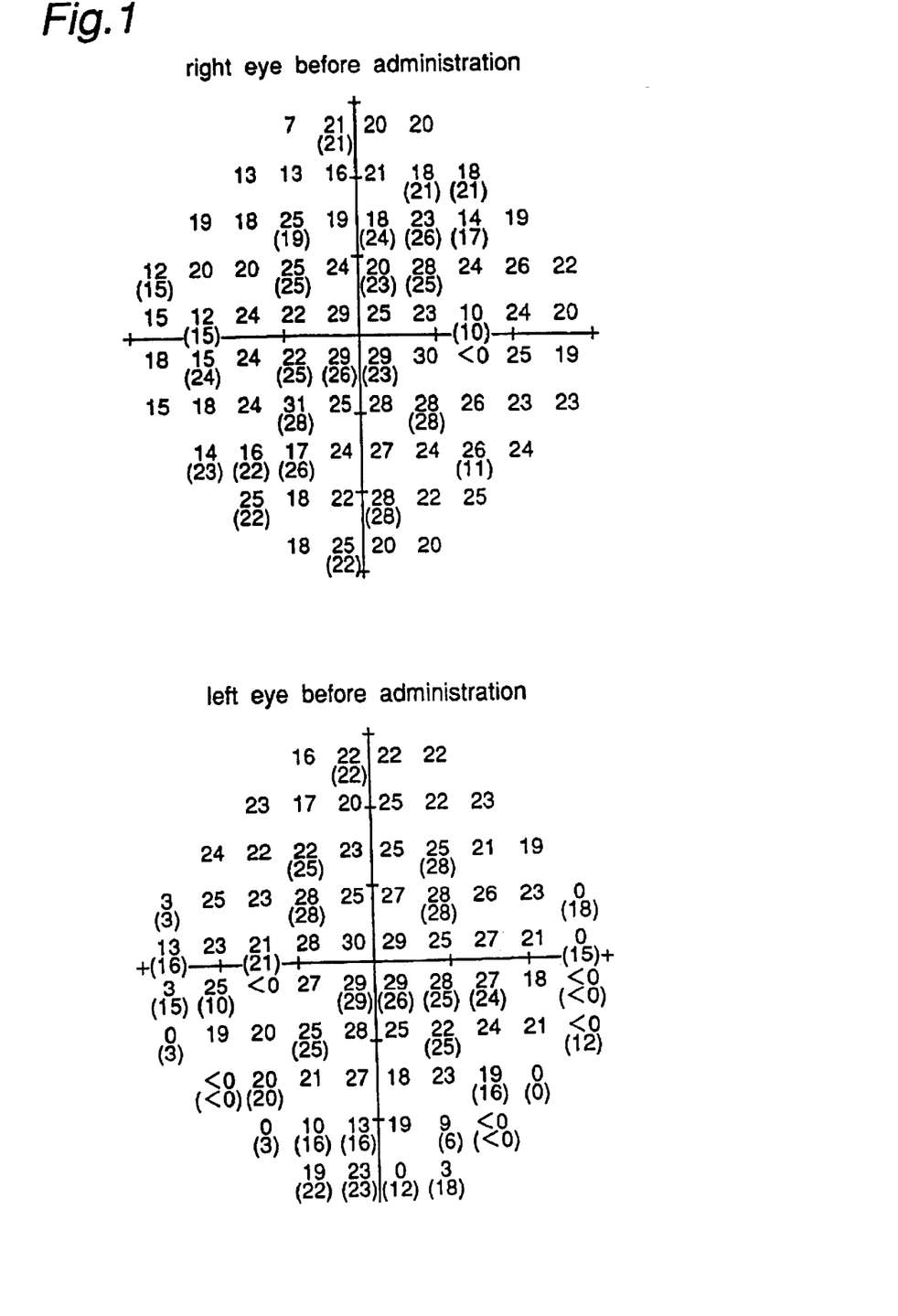
FIG. 1 shows maps of found thresholds measured by Humphrey perimeter before administration in Example 2.
Figure 2:
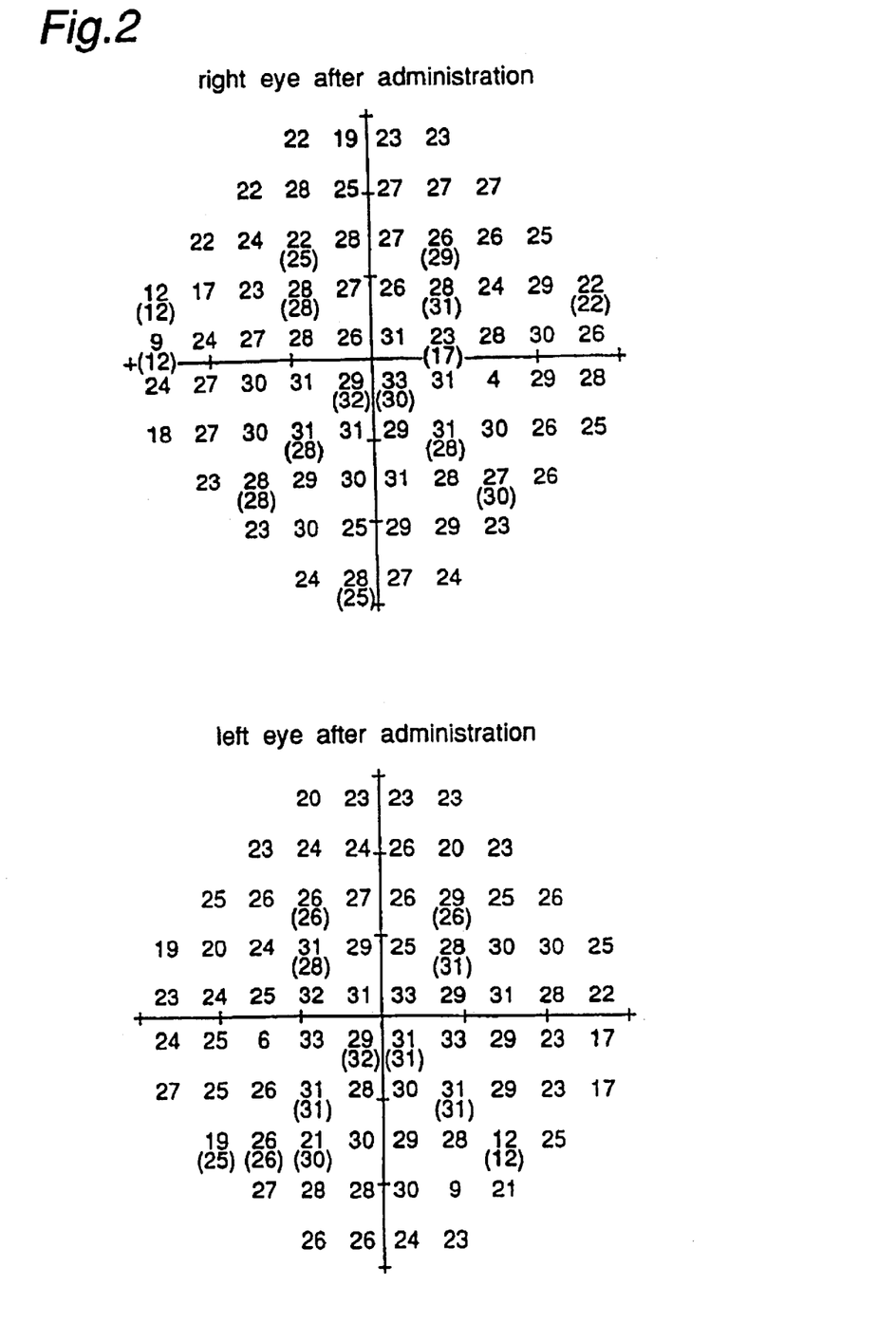
FIG. 2 shows maps of found thresholds measured by Humphrey perimeter after administration in Example 2.

The found thresholds are shown in FIG. 1 and FIG. 2. In FIG. 1 and FIG. 2, numerical data indicate sensitivities in dB at measuring positions within 30 degrees of center angle.

As shown above, a significant improvement in visual field was recognized from the results of measurement by Humphrey perimeter.

Example 3

A patient (female, 66 years old) received twice a day administration of the same Rescula eye drops as that in Example 1 for 2 months.

Figure 3:
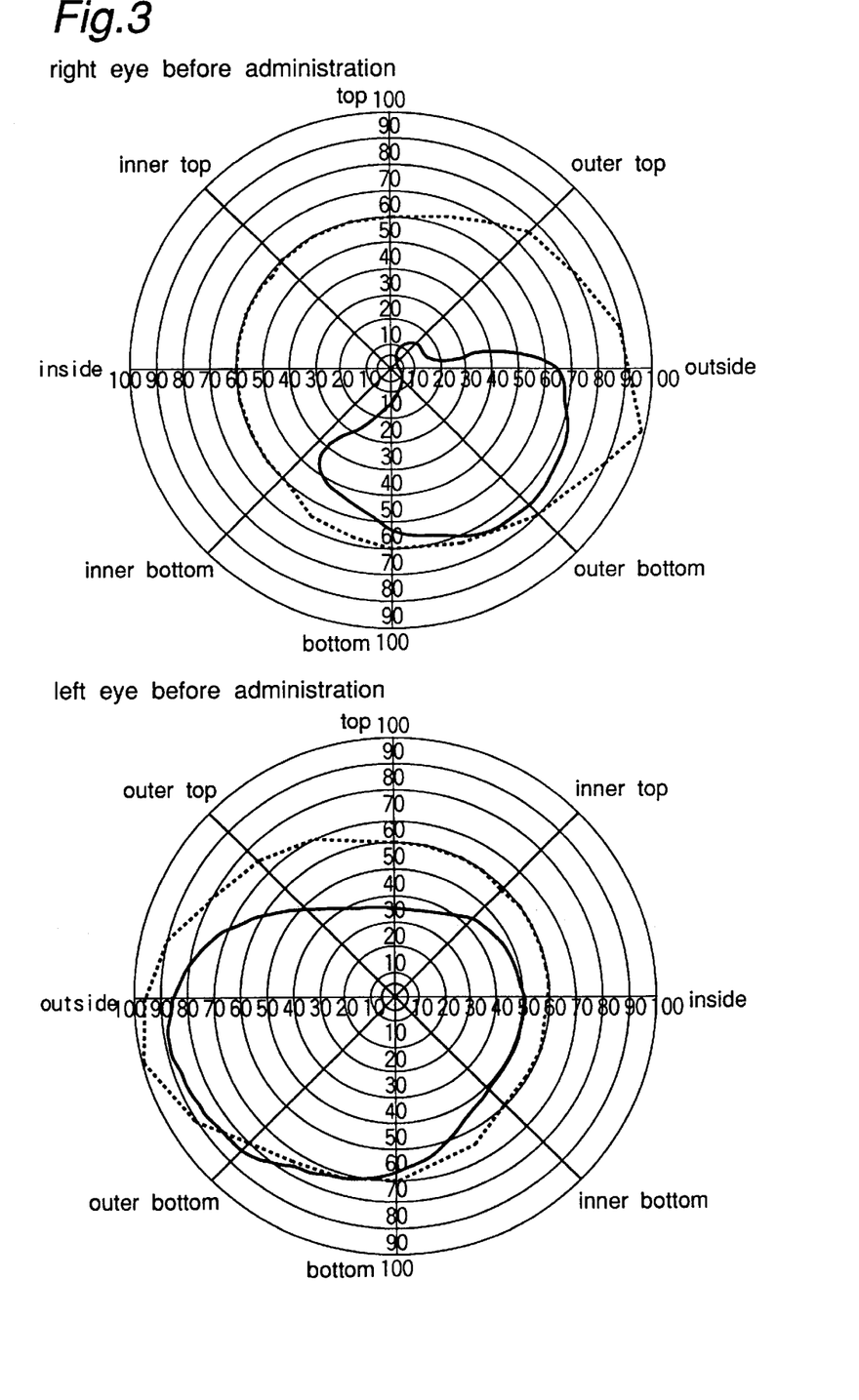
FIG. 3 shows maps of visual fields measured by Goldmann perimeter before administration in Example 3.
Figure 4:
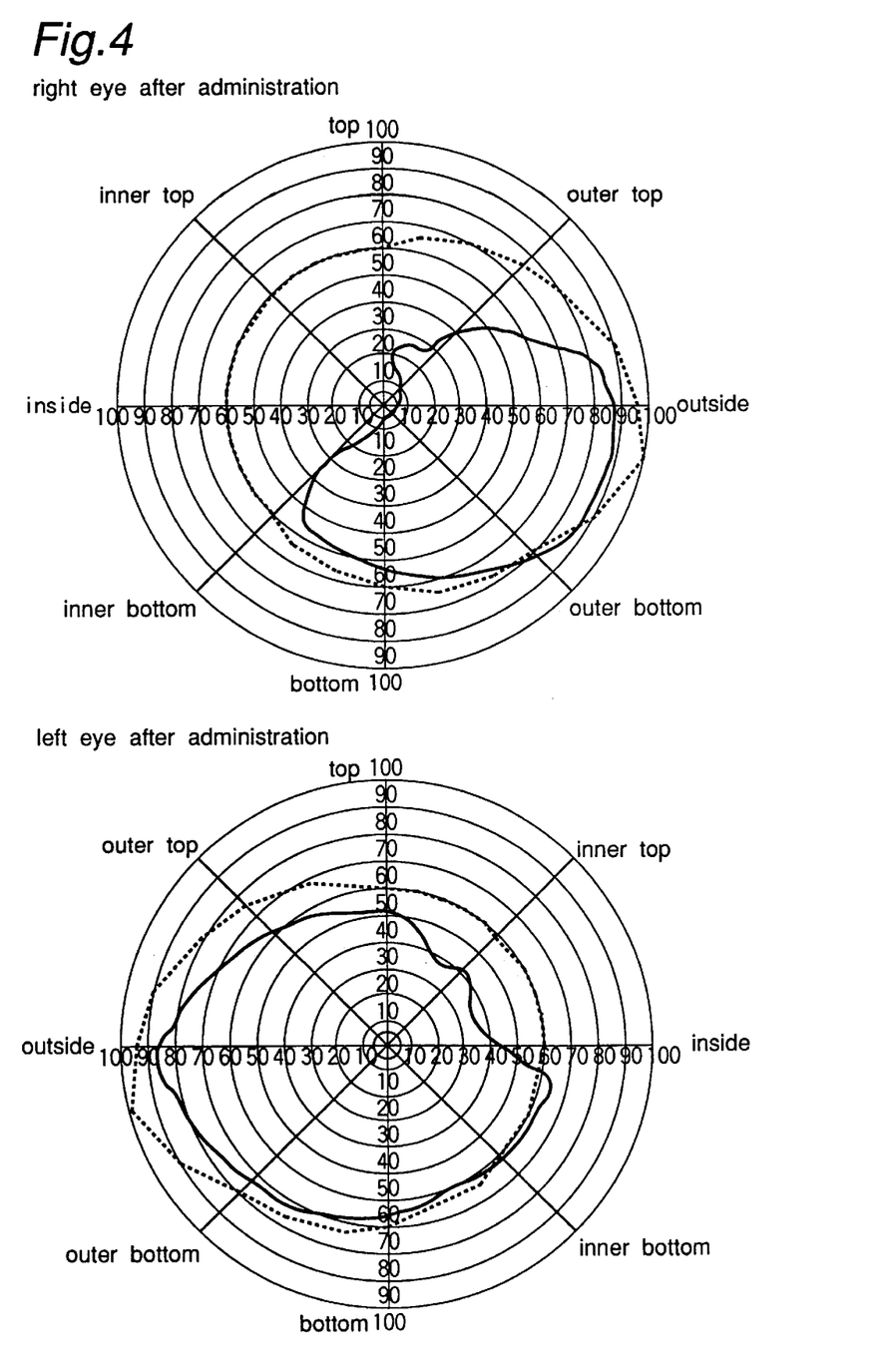
FIG. 4 shows maps of visual fields measured by Goldmann perimeter after administration in Example 3.

Conditions of visual fields before and after administration were measured using a Goldmann perimeter. The results of peripheral visual field obtained using V/4 are shown in FIG. 3 and FIG. 4. In FIG. 3 and FIG. 4, the dotted lines indicate the mean residual visual field of healthy Japanese. The angles (in degree) of the said residual visual field are shown in Table 3.

TABLE 3

| top | outer top | outside | outer bottom | bottom | inner bottom | inside | inner top | total | visual efficiency |
| --- | --- | --- | --- | --- | --- | --- | --- | --- | --- |
| 60 | 75 | 95 | 80 | 70 | 60 | 60 | 60 | 560 | 100% |

Note: visual efficiency = total angle ÷ 560 × 100

In FIG. 3 and FIG. 4, the heavy lines indicate the residual visual field of the patient.

The results show that the V/4 area enlarged and scotoma disappeared. From the results, visual efficiencies before and after administration were calculated according to "guideline for recognition of visual field disorder" (Ministry of Health and Welfare). The area of the residual visual field was calculated from the results. The area was measured by a planimeter (PLANIX 5000 available from Tamaya Keisoku System K.K.). The results are shown in Table 4.

TABLE 4

|  | top | outer top | outside | outer bottom | bottom | inner bottom | inside | inner top | total | visual efficiency | area (cm$^2$) |
| --- | --- | --- | --- | --- | --- | --- | --- | --- | --- | --- | --- |
| Before administration |
| right eye | 0 | 15 | 62 | 75 | 65 | 0 | 0 | 0 | 217 | 38.75% | 72.83 |
| left eye | 35 | 48 | 85 | 84 | 67 | 52 | 48 | 43 | 462 | 82.50% | 166.52 |
| After administration |
| right eye | 0 | 40 | 88 | 83 | 65 | 40 | 0 | 0 | 316 | 56.43% | 117.46 |
| left eye | 52 | 62 | 85 | 78 | 65 | 63 | 42 | 40 | 487 | 86.96% | 180.76 |

Note: visual efficiency = total angle of the residual visual field ÷ 560 × 100

Intraocular pressures (I.O.P.) before the administration were 20 mm Hg in both right and left eyes and I.O.P. after the administration were 20 mm Hg in both right and left eyes. Therefore almost no effect was present in respect of I.O.P.

As shown above, a significant improvement in visual field was recognized from the results of measurement by Goldmann perimeter.

Example 4

A patient (female, 49 years old, only the left eye was ill) received twice a day administration of the same Rescula eye drops as that in Example 1 for 4 months.

Figure 5:
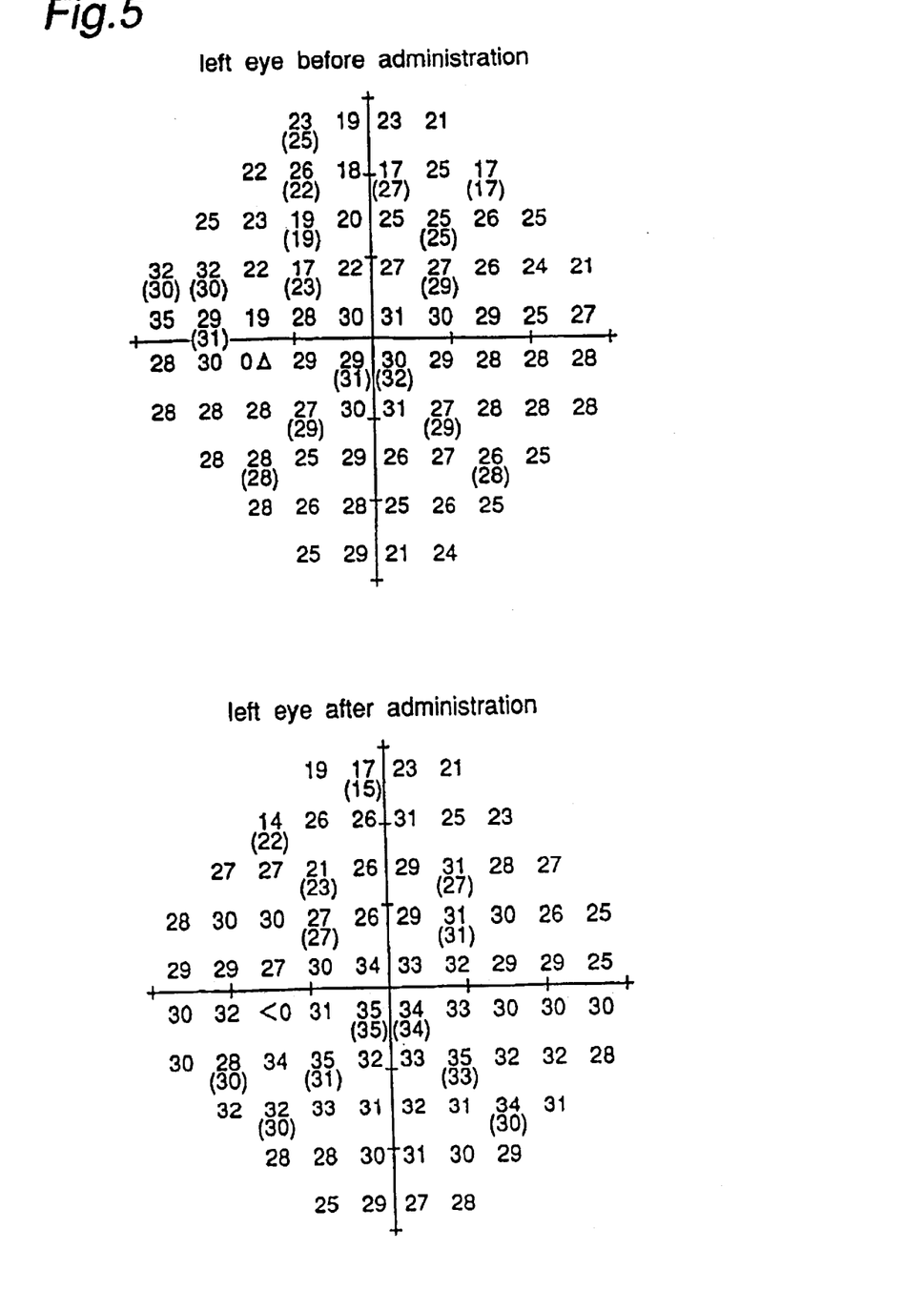
FIG. 5 shows maps of found thresholds measured by Humphrey perimeter before and after administration in Example 4.

Conditions of visual fields before and after administration were measured using a Humphrey perimeter. The obtained "global indices" are shown in Table 5. The found thresholds are shown in FIG. 5.

TABLE 5

| (Global Index) | | |
| --- | --- | --- |
|  | left eye before administration | left eye after administration |
| MD | −2.77 DB | +0.70 DB |
| CPSD | 1.90 DB | 1.14 DB |

As shown above, a significant improvement in visual field was recognized from the results of measurement by Humphrey perimeter. The MD for global index after administration was within the normal range.

Example 5

A patient (male, 23 years old, Leber's disease) received twice a day administration of Rescula eye drops of the Example 1 (0.12%) for 9 months.

Recovery of visual acuity (V.A.) was observed apparent from the results of measurement of before and after the administrations, which are shown in Table 6.

TABLE 6

|  | right eye | left eye |
| --- | --- | --- |
| V.A. before administration (corrected eye) | 0.04 | 0.06 |
| V.A. after administration (corrected eye) | 0.08 | 0.4 |

Example 6

A patient (female, 13 years old, pigmentary retinal degeneration) received twice a day administration of the same Rescula eye drops as that in Example 1 for 4 months.

Figure 6:
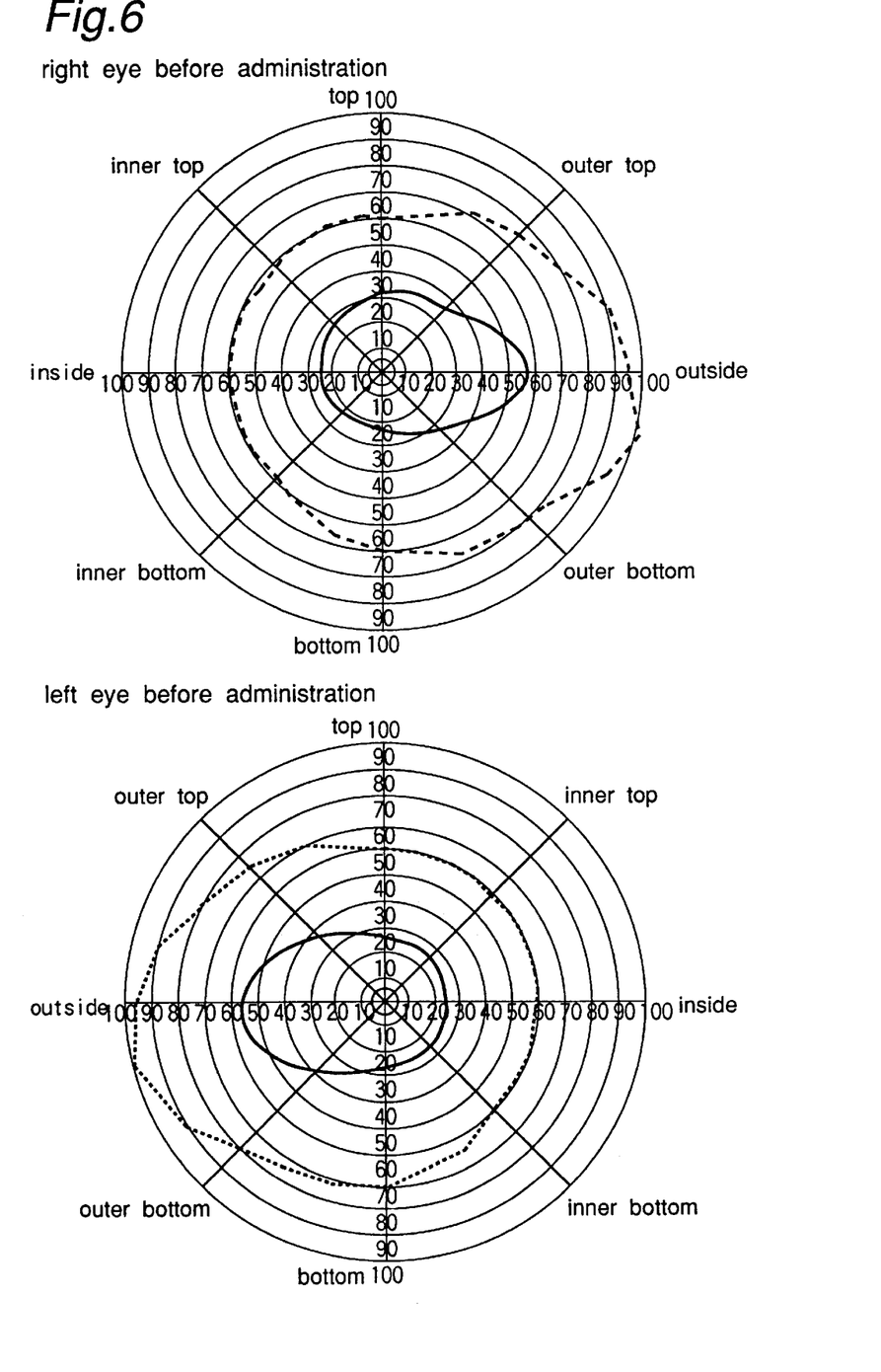
FIG. 6 shows maps of visual fields measured by Goldmann perimeter before administration in Example 6.
Figure 7:
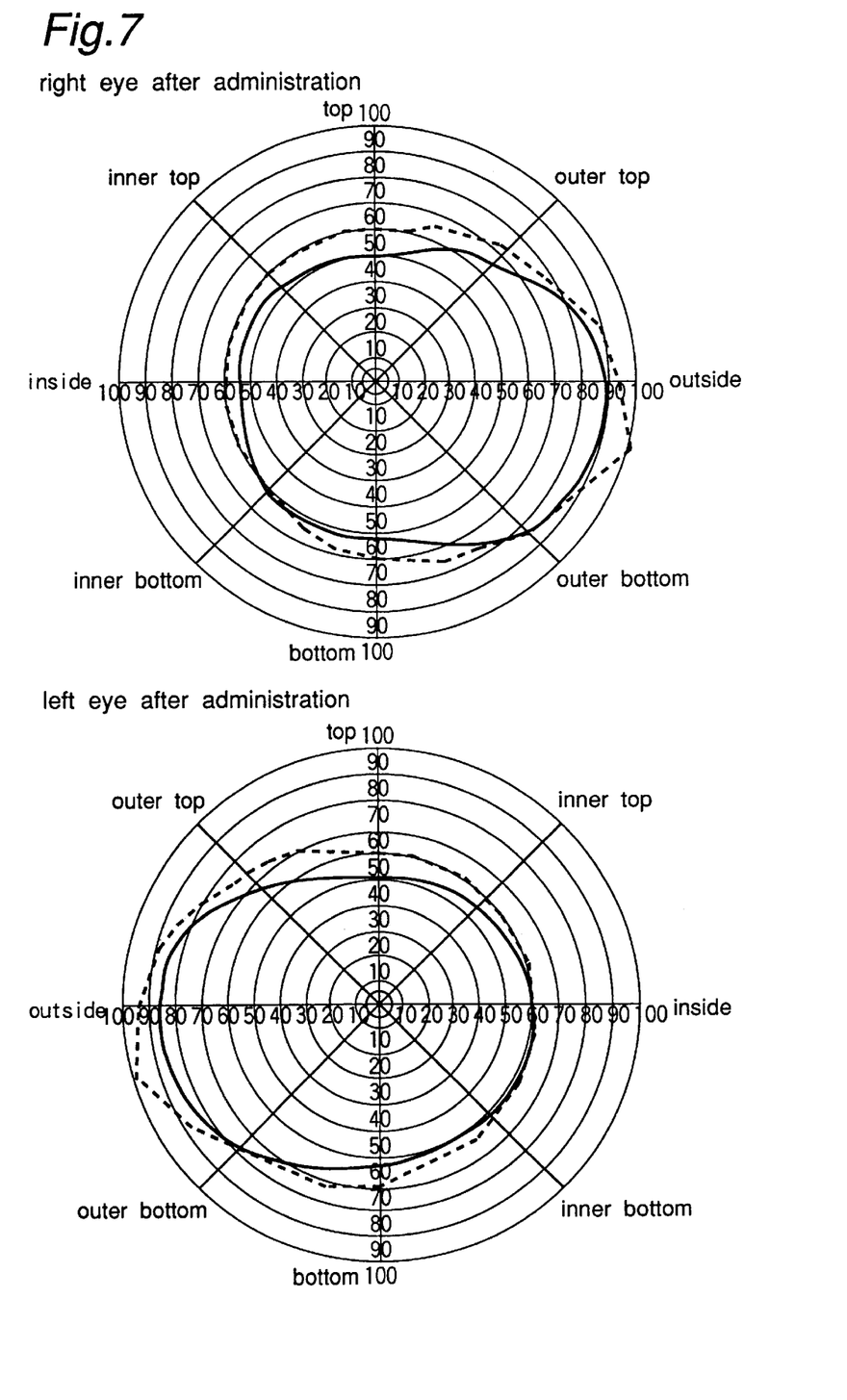
FIG. 7 shows maps of visual fields measured by Goldmann perimeter after administration in Example 6.

Conditions of visual fields before and after administration were measured using a Goldmann perimeter. The results of peripheral visual field obtained using V/4 are shown in FIG. 6 and FIG. 7.

The visual efficiency and the area of the residual visual field were obtained from the results according to the same manner as in Example 3. The results were shown in Table 7.

TABLE 7

|  | top | outer top | outside | outer bottom | bottom | inner bottom | inside | inner top | total | visual efficiency | area (cm$^2$) |
| --- | --- | --- | --- | --- | --- | --- | --- | --- | --- | --- | --- |
| Before administration |
| right eye | 30 | 36 | 58 | 30 | 20 | 21 | 27 | 30 | 252 | 45.00% | 47.87 |
| left eye | 25 | 34 | 57 | 33 | 23 | 22 | 23 | 26 | 243 | 43.39% | 45.57 |
| After administration |
| right eye | 52 | 69 | 90 | 82 | 60 | 60 | 55 | 55 | 523 | 93.39% | 202.06 |
| left eye | 50 | 63 | 90 | 80 | 62 | 60 | 60 | 57 | 522 | 93.21% | 200.08 |

As apparent from the above results of the measurement by Goldmann perimeter clear recovery of the visual field was observed.

Example 7

A patient (male, 14 years old, pigmentary retina degeneration) received twice a day administration of the same Rescula eye drops as that in Example 1 for 4 months.

Figure 8:
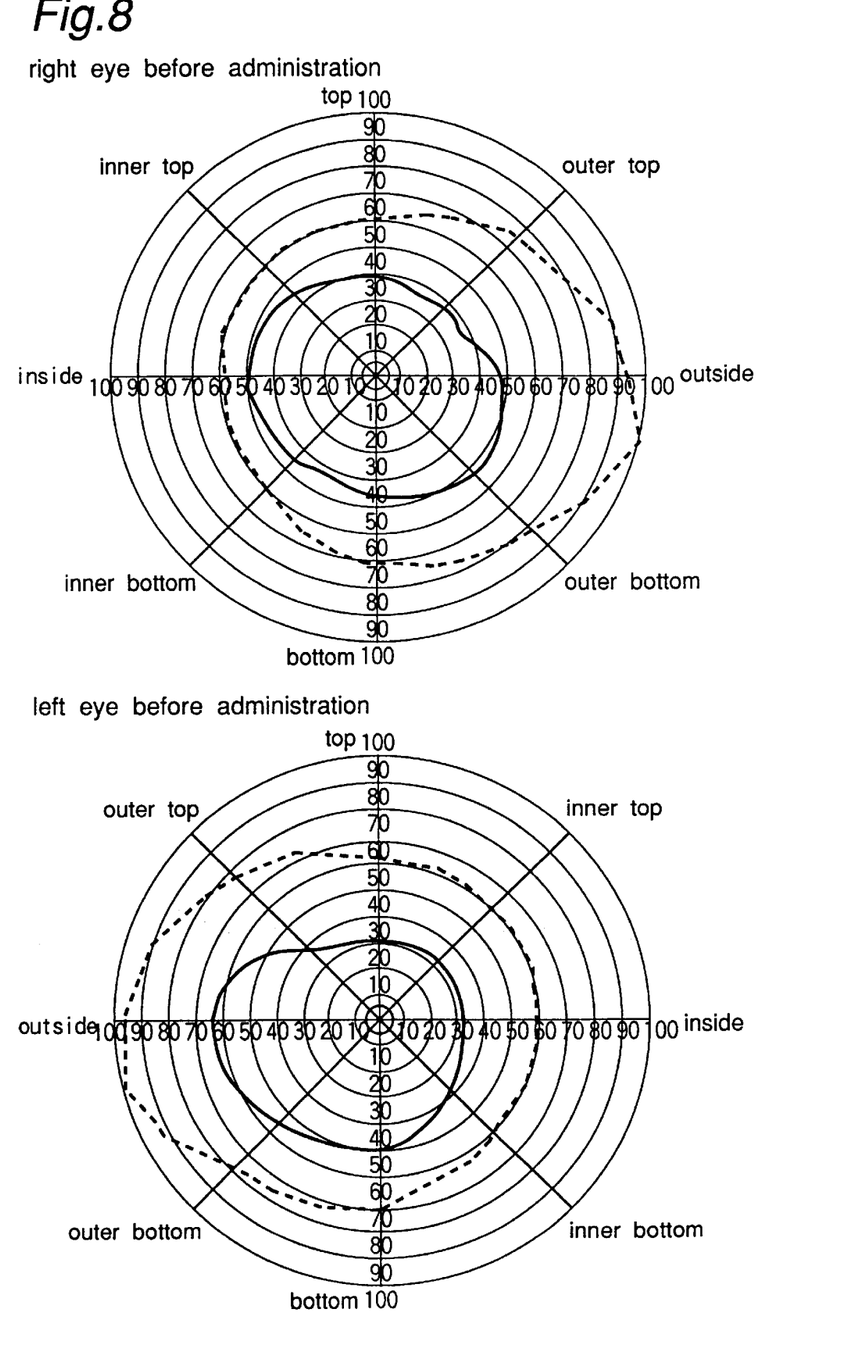
FIG. 8 shows maps of visual fields measured by Goldmann perimeter before administration in Example 7.
Figure 9:
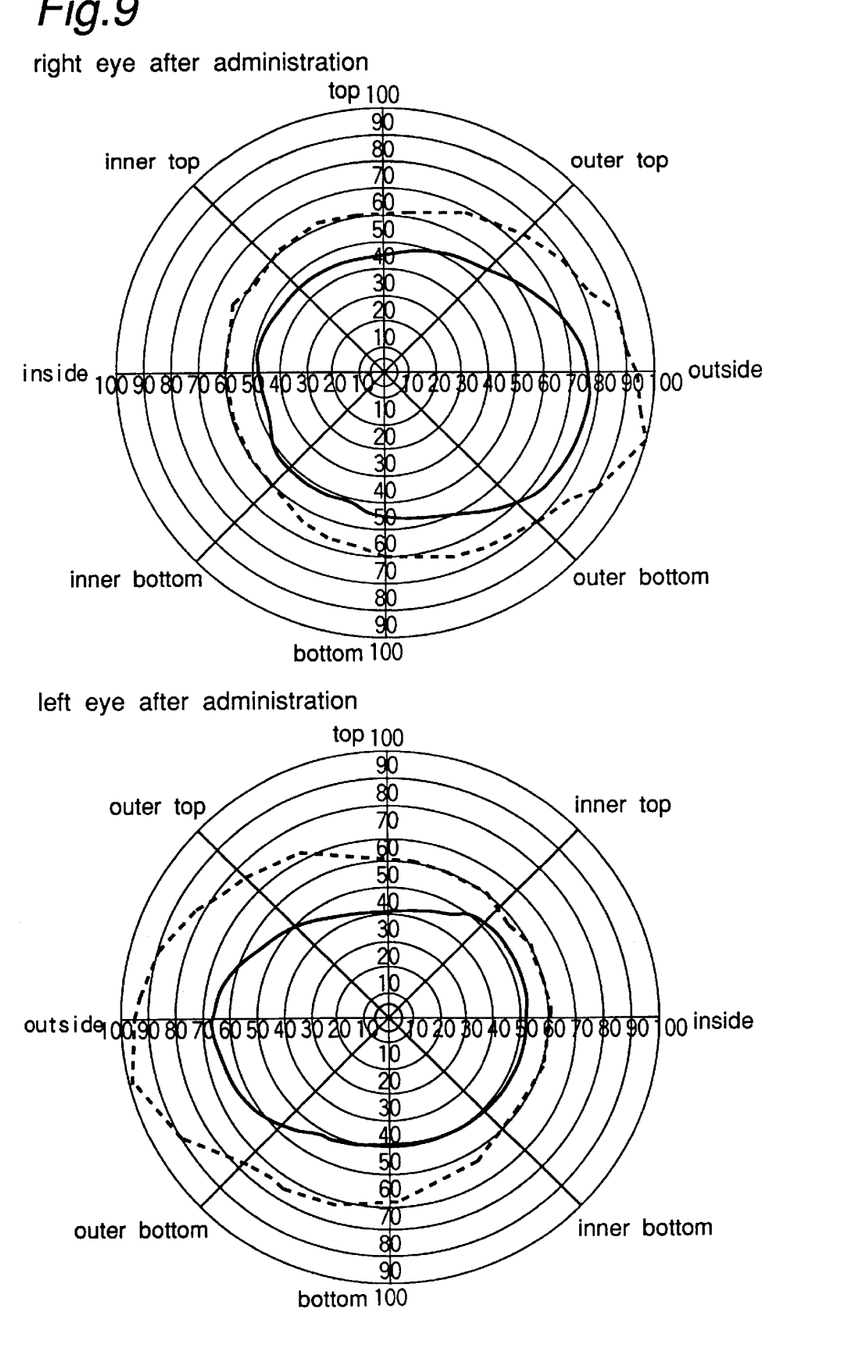
FIG. 9 shows maps of visual fields measured by Goldmann perimeter after administration in Example 7.

Conditions of visual fields before and after administration were measured using a Goldmann perimeter. The results of peripheral visual field obtained using V/4 are shown in FIG. 8 and FIG. 9.

The visual efficiency and the area of the residual visual field were obtained from the results according to the same manner as in Example 3. The results were shown in Table 8.

TABLE 8

| | top | outer top | outside | outer bottom | bottom | inner bottom | inside | inner top | total | visual efficiency | area (cm$^2$) |
|---|---|---|---|---|---|---|---|---|---|---|---|
| | | | | Before administration | | | | | | | |
| right eye | 38 | 35 | 47 | 48 | 45 | 41 | 50 | 43 | 347 | 61.96% | 84.23 |
| left eye | 30 | 37 | 62 | 54 | 47 | 34 | 30 | 31 | 325 | 58.04% | 80.48 |
| | | | | After administration | | | | | | | |
| right eye | 45 | 55 | 78 | 70 | 55 | 52 | 48 | 46 | 449 | 80.18% | 144.24 |
| left eye | 40 | 47 | 64 | 58 | 47 | 47 | 51 | 50 | 404 | 72.14% | 114.78 |

As apparent from the above results of the measurement by Goldmann perimeter clear recovery of the visual field was observed.

Example 8
(Disorder models of rats suffered from retinal photoreceptor cell)
Breeding Condition SD type rats (male, 11 weeks old, 310 to 360 g) were bred as lit up with light at 800 to 1200 Lux for 4 days continuously. These rats were grouped to Test Groups II–V according to test conditions.

Other one group (Test Group I) of SD type rats was bred for 4 days as lit up with fluorescent light of not more than 300 Lux under 12 hours interval of light and dark, which is referred as a normal control.
Test Conditions The test groups, test drugs, concentration and the animal numbers are shown in Table 9.

TABLE 9

| test group | test drugs | concentration | numbers |
|---|---|---|---|
| Group I | normal control | — | 4 |
| Group II | disorder control | base only | 3 |
| Group III | Test drug 1 | 0.12% | 3 |
| Group IV | Test drug 2 | 0.1% | 3 |
| Group V | Test drug 3 | 0.006% | 3 |

Administration

The rats received three times a day administration of the test drug by 5 µl/eye/one time in the both eyes at 10:00, 13:00 and 16:00 o'clock during lighting. The rats of Group II received only the base.
Preparation of Samples The rats were killed by ether anesthesia on the next day of the final day of the lighting, the both eyes of the killed rats were extracted, and the eyes were immediately dipped in a fixative liquid of a phosphate buffer solution containing 2% paraformaldehyde and 2.5% glutaraldehyde. After 2 hours the corneas were cut off by a razor to remove the crystallines, and the remaining tissue were subjected with fixation in the same fixative liquid over one night.

The fixed tissues were treated with alcoholic solution containing ethanol (70 to 100%) and embedded with paraffine.

The tissue fragments were cut parallel along the ophthalmus meridiam to make three slices of retina containing an optic disk per one eye.

The retina slices were dyed by hematoxylin and Eosin stain.
Determination of the Cell Layer The dyed retina slices were observed at 100 magnification by an optical microscope, and photographed on positive films (RDPII 135, available from Fuji Photofilm K.K.) to determine the thickness of the cell layer from the outer nuclear layer to the outer segment in order to calculate the actual thickness of the cell layer. The results are shown in Table 10.

TABLE 10

| test group | test drugs | cell layer average thickness (µm') ± SD |
|---|---|---|
| Group I | normal control | 70.7 ± 3.5 |
| Group II | disorder control | 34.9 ± 0.8 |
| Group III | Test drug 1 | 42.6 ± 2.9 * |
| Group IV | Test drug 2 | 41.0 ± 3.6 |
| Group V | Test drug 3 | 48.8 ± 4.8 ** |

*: $0.01 < P < 0.05$
**: $p < 0.01$ according to Dunnett Test
Test drug 1: 13,14-dihydro-15-keto-20-ethyl-PGF2α isopropyl ester
Test drug 2: 13,14-dihydro-18,19,20-trinor-17-phenyl-PGF2α isopropyl ester
Test drug 3: 2-decarboxy-2-(2-carboxyethyl)-13,14-dihydro-15-keto-16,16-difluoro-20-ethyl-PGE1 isopropyl ester The each test drug was dissolved in following base at a given concentration, and dropped to eyes.

| Base Formulation | |
|---|---|
| Polysolvate 80 | 5 g |
| NaCl | 3 g |

The aboves were made up to 500 ml by sterilized distilled water.

Apparent from the above results the optic nerve caused by lighting is effectively cured by the above test drugs.

What is claimed is:

1. A method for treatment of optic nerve disorder wherein visual field is contracted, or visual acuity is damaged, or retinal photo receptor cells may be damaged which comprises administering, to a subject in need of such treatment, a prostanoic acid compound of the formula (I) in an amount effective for relieving contraction of visual field, or for relieving damage of visual acuity, or for protecting retinal photo receptor cells wherein X and Y are hydrogen, hydroxy, halogen, lower alkyl, hydroxy(lower)alkyl or oxo with the proviso that at least one of X and Y is a group other than hydrogen and that the five-membered ring may have at least one double bond, A is COOH, a salt or ester thereof, B is —CH—CH$_2$—, —CH=CH, or —C≡C—, z is wherein R$_3$ is lower alkyl or hydrogen R$_1$ is a bivalent saturated or unsaturated, lower or medium aliphatic hydrocarbon residue which is unsubstituted or substituted with halogen, oxo or aryl, and R$_1$ is a saturated or unsaturated, lower or medium aliphatic hydrocarbon residue which is unsubstituted or substituted with oxo, hydroxy, halogen, lower alkoxy, lower alkanoyloxy, cyclo(lower)alkyl, aryl or aryloxy.

2. A method according to claim 1, in which the said prostanoic acid compound is 15-keto-prostaglandin compound.

3. A method according to claim 1, in which the said prostanoic acid compound is 15-keto-prostaglandin F compound.

4. A method according to claim 1, in which the said prostanoic acid compound is 13,14-dihydro-15-keto-prostaglandin compound.

5. A method according to claim 1, in which the said prostanoic acid compound is 13,14-dihydro-15-keto-prostaglandin F compound.

6. A method according to claim 1, in which the said prostanoic acid compound is 13,14-dihydro-15-keto-20-lower-alkyl prostaglandin compound.

7. A method according to claim 1, in which the said prostanoic acid compound is 13,14-dihydro-15-keto-20-lower-alkyl-prostaglandin F compound.

8. A method according to claim 1, in which the said prostanoic acid compound is 13,14-dihydro-15-keto-20-ethyl-prostaglandin compound.

9. A method according to claim 1, in which the said prostanoic acid compound is 13,14-dihydro-15-keto-20-ethyl-prostaglandin F compound.

10. A method according to claim 1, in which the said prostanoic acid compound is administered in the form of eye drops.

11. A method according to claim 1 for relieving contraction of visual field.

12. A method according to claim 1 for relieving damage of visual acuity.

13. A method according to claim 1, in which the optic nerve disorder is selected from the group consisting of retinal optic nerve disorder, inflammatory optic nerve disorder, simple optic nerve disorder, axial optic nerve disorder, glaucomatous optic nerve disorder and hemianoptic optic nerve disorder.

14. A method according to claim 1 wherein the optic nerve disorder is caused by a disease selected from the group consisting of central serous chorioretinopathy, central serous chorioretinitis, hypertensive retinopathy, senile ocular fundus, arteriosclerotic retinopathy, renal retinopathy, diabetic retinopathy, retinal artery occlusion, retinal vein occlusion, retinal detachment, pigmentary retinal degeneration, retinopathy of prematurity, anemic retinopathy, leukemic retinopathy, retinochoroidal disorder by trauma, optic neuritis, papillitis, arachnoiditis, Leber's disease and myelitis.

15. A method according to claim 1, in which said prostanoic acid compound is a 13,14-dihydro-prostaglandin compound.

16. A method according to claim 1, for protecting retinal photo receptor cells.

17. A method according to claim 1, wherein R$_1$ is a straight or branched chain hydrocarbonyl group having 1–14 carbon atoms which is unsubstituted or substituted with halogen, oxo or aryl, and R$_2$ is a straight or branched chain hydrocarbonyl group having 1–14 carbon atoms which is unsubstituted or substituted with oxo, hydroxy, halogen, lower alkoxy, lower alkanoyloxy, cyclo(lower)alkyl, aryl or aryloxy.

* * * * *